(12) United States Patent
Fujisaki et al.

(10) Patent No.: US 10,278,876 B2
(45) Date of Patent: May 7, 2019

(54) MALE SURFACE FASTENER

(71) Applicant: YKK Corporation, Tokyo (JP)

(72) Inventors: Ayumi Fujisaki, Toyama (JP); Masayuki Naohara, Toyama (JP)

(73) Assignee: YKK Corporation (JP)

(*) Notice: Subject to any disclaimer, the term of this patent is extended or adjusted under 35 U.S.C. 154(b) by 501 days.

(21) Appl. No.: 14/437,149

(22) PCT Filed: Oct. 26, 2012

(86) PCT No.: PCT/JP2012/077772
§ 371 (c)(1),
(2) Date: Apr. 20, 2015

(87) PCT Pub. No.: WO2014/064842
PCT Pub. Date: May 1, 2014

(65) Prior Publication Data
US 2015/0272790 A1    Oct. 1, 2015

(51) Int. Cl.
A44B 18/00    (2006.01)
A61F 13/56    (2006.01)
A61F 13/62    (2006.01)

(52) U.S. Cl.
CPC ........ A61F 13/627 (2013.01); A44B 18/0065 (2013.01); A61F 13/5633 (2013.01); A61F 13/625 (2013.01); Y10T 24/2767 (2015.01)

(58) Field of Classification Search
CPC . A61F 13/627; A61F 13/5633; A44B 18/0065
See application file for complete search history.

(56) References Cited

U.S. PATENT DOCUMENTS

2002/0124359 A1* 9/2002 Murasaki ........... A44B 18/0049
24/452
2003/0106188 A1 6/2003 Armela et al.
(Continued)

FOREIGN PATENT DOCUMENTS

GB    2375141 A    11/2002
JP    2002-262908 A    9/2002
(Continued)

OTHER PUBLICATIONS

Supplementary European Search Report, European Patent Application No. 12887076.3, dated Apr. 14, 2016.
(Continued)

Primary Examiner — Benjamin J Klein
Assistant Examiner — Sara A Sass
(74) Attorney, Agent, or Firm — Kilpatrick Townsend & Stockton LLP

(57) ABSTRACT

A male surface fastener has a sheet having a main surface, and a group of engagement elements in which the engagement elements are regularly arranged, the engagement element having a pillar that stands on the main surface of the sheet and an engagement head that is expanded along the main surface from the top end of the pillar, wherein $0.05 \leq S2/S1 \leq 0.15$ is satisfied where S1 represents an area of the main surface which corresponds to a region in which the group of engagement elements is arranged, and S2 represents a sum of areas of the top surfaces of the engagement heads of the engagement elements of the group of engagement elements.

9 Claims, 11 Drawing Sheets

(56) References Cited

U.S. PATENT DOCUMENTS

| | | | |
|---|---|---|---|
| 2004/0031130 A1* | 2/2004 | Clarner | A44B 18/0049 24/452 |
| 2005/0079321 A1 | 4/2005 | Tuman et al. | |
| 2005/0081344 A1 | 4/2005 | Clarner | |
| 2007/0275622 A1* | 11/2007 | Masuda | A61F 13/62 442/327 |
| 2009/0013506 A1* | 1/2009 | Mizuhara | A44B 18/0069 24/442 |
| 2014/0338159 A1* | 11/2014 | Sakaguchi | A44B 18/0019 24/442 |

FOREIGN PATENT DOCUMENTS

| | | |
|---|---|---|
| JP | 2007-044139 A | 2/2007 |
| JP | 2010-075541 A | 4/2010 |
| JP | 2010-125158 A | 6/2010 |
| WO | 2005/027675 A1 | 3/2005 |

OTHER PUBLICATIONS

International Search Report, PCT Patent Application No. PCT/JP2012/077772, dated Jan. 22, 2013.
International Preliminary Report on Patentability, PCT Patent Application No. PCT/JP2012/077772, dated May 7, 2015.
Office Action, Japanese Patent Application No. 2014-543109, dated Apr. 5, 2016.

\* cited by examiner

MALE SURFACE FASTENER

This application is a national stage application of PCT/JP2012/077772, which is incorporated herein by reference.

TECHNICAL FIELD

The present invention relates to a male surface fastener, a diaper, and a securing method.

BACKGROUND ART

The patent document 1 discloses a surface fastener 10 that is provided with engagement elements 20 each having a first pillar 21a and a second pillar 21b which are arranged to be crossed and form a cross-shaped pillar 21 onto which a plate-like thin engagement head 22 is coupled.

CITATION LIST

Patent Literature

[PTL 1] Japanese Patent Application Laid-open No. 2002-262908

SUMMARY OF INVENTION

Technical Problem

The number of the engagement elements per unit area may be increased in an effort to enhance the engagement power of the surface fastener. However, according to an analysis made by the present inventors, it has been turned out that satisfactory outcomes are not always obtained in some cases despite that the number of the engagement elements per unit area was increased.

Solution to Problem

A male surface fastener according to the present invention comprises:
  a sheet having a main surface; and
  a group of engagement elements in which the engagement elements are regularly arranged, the engagement element having a pillar that stands on the main surface of the sheet and an engagement head that is expanded along the main surface from the top end of the pillar, wherein $0.05 \leq S2/S1 \leq 0.15$ is satisfied where
  S1 represents an area of the main surface which corresponds to a region in which the group of engagement elements is located, and
  S2 represents a sum of areas of the top surfaces of the engagement heads of the engagement elements of the group of engagement elements.

According to the present configuration, a case where preferable result is not obtainable with high possibility even though the number of the engagement elements was increased may be remedied preferably.

The pillar may have a first pillar and a second pillar which are crossed over the main surface so that the pillar is shaped like a cross in section, and the engagement head may be a plate-like thin portion having a pair of expanded portions expanding from the pillar along the elongation direction of the first pillar. Under this configuration, an increased pang against a human skin may not be evident even the height of the engagement element was increased. The strength of the pillar may be suitably secured by adjusting the length and the width of the pillar corresponding to the area/region of the top surface of the engagement head.

The engagement elements may be arranged at regular intervals in a first direction along the main surface and in a second direction along the main surface and perpendicular to the first direction.

$W20 < D20$ may be satisfied where $D20$ represents a separation distance between the adjacent engagement heads along the first direction, and $W20$ represents the maximum width of the engagement head along the first direction.

$W30 < D30$ may be satisfied where $D30$ represents a separation distance between the adjacent engagement heads along the second direction, and $W30$ represents the maximum width of the engagement head along the second direction.

The maximum width $W20$ may satisfy $0.2 \text{ mm} < W20 < 0.4 \text{ mm}$ or the separation distance $D20$ may satisfy $0.6 \text{ mm} < D20 < 1.0 \text{ mm}$.

The maximum width $W30$ may satisfy $0.15 \text{ mm} < W30 < 0.35 \text{ mm}$ or the separation distance $D30$ may satisfy $0.35 \text{ mm} < D30 < 0.75 \text{ mm}$.

The arrangement interval $P20$ for the adjacent engagement elements in the first direction may satisfy $1.0 \text{ mm} \leq P20 \leq 1.2 \text{ mm}$.

The arrangement interval $P30$ for the adjacent engagement elements in the second direction may satisfy $0.7 \text{ mm} \leq P30 \leq 0.9 \text{ mm}$.

A diaper according to the present invention comprises: a diaper body comprising a front covering that covers the lower trunk of a human from a front side, a back covering that covers the lower trunk of a human from a rear side, and a bottom covering that is provided between the front covering and the back covering and covers the crotch of a human from underneath; and
  a male surface fastener directly or indirectly provided on at least one of the front covering and the back covering of the diaper body, wherein the male surface fastener comprises:
  a sheet having a main surface; and
  a group of engagement elements in which the engagement elements are regularly arranged, the engagement element having a pillar that stands on the main surface of the sheet and an engagement head that is expanded along the main surface from the top end of the pillar, wherein $0.05 \leq S2/S1 \leq 0.15$ is satisfied where
  S1 represents an area of the main surface which corresponds to a region where the group of engagement elements is located, and
  S2 represents a sum of areas of the top surfaces of the engagement heads of the engagement elements of the group of engagement elements.

The respective external surfaces of the front covering and the back covering of the diaper body may be configured to include a nonwoven fabric.

A securing method according to the present invention comprises:
  grasping a male surface fastener directly or indirectly, the male surface fastener comprising:
  a sheet having a main surface; and
  a group of engagement elements where the engagement elements are regularly arranged, the engagement element having a pillar that stands on the main surface of the sheet and an engagement head that is expanded along the main surface from the top end of the pillar, wherein $0.05 \leq S2/S1 \leq 0.15$ is satisfied where S1 represents an area of the main surface which corresponds to a region in which the group of engagement elements is arranged, and S2 represents a sum of areas of the top surfaces of the engagement heads of the engagement elements of the group of engagement elements; and pushing the male surface fastener against the female surface fastener so that the male surface faster engages with the female surface fastener.

The step of grasping may not be limited to be performed by a human but may be preformed by a humanoid or industrial robot where no physical contact may not be required. The configuration of the female surface fastener may be arbitrary.

The male surface fastener may be directly or indirectly provided on at least one of a front covering and a back covering of a diaper, the diaper comprising the front covering that covers the lower trunk of a human from the front side, the back covering that covers the lower trunk of a human from the rear side, and a bottom covering that is provided between the front covering and the back covering and covers the crotch of a human from the underneath, and wherein the female surface fastener with which the male surface fastener engages may be a nonwoven fabric forming the other of the front covering and the back covering of the diaper.

Advantageous Effects of Invention

According to the present invention, appropriate engagement power of the surface fastener can be preferably secured.

DESCRIPTION OF EMBODIMENTS

Hereinafter, embodiments of the present invention will be described with reference to drawings. The embodiments are not mutually exclusive, and the skilled person in the art would be able to appropriately combine them and be able to expect resulting synergetic effect of such a combination without excessive descriptions. The duplicative descriptions among embodiments will be omitted basically. The referenced drawings are mainly for the illustration of the present invention and they may be simplified accordingly.

First Embodiment

Figure 1:
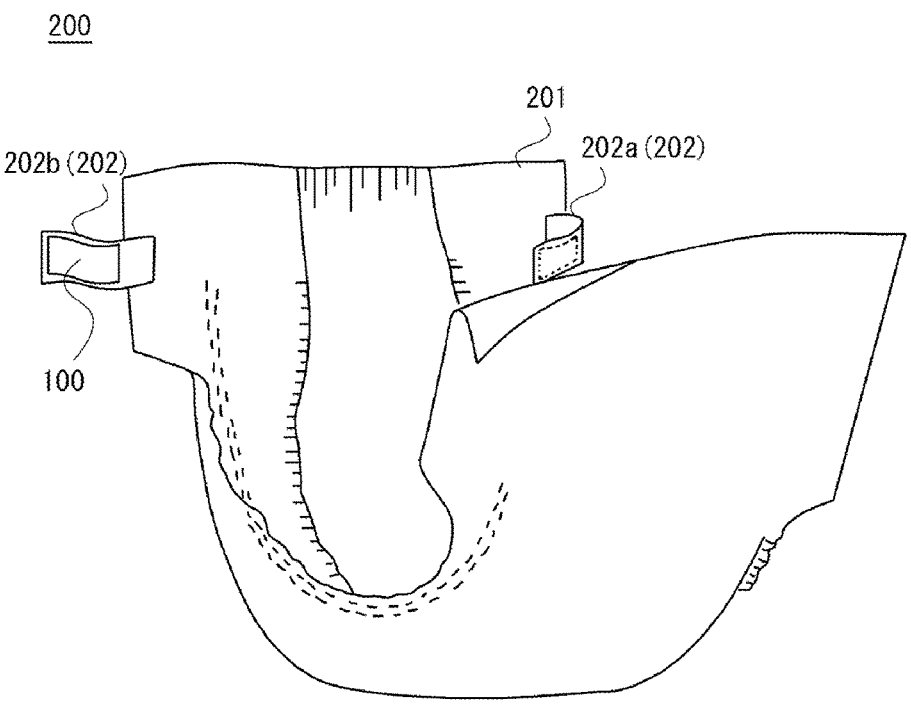
FIG. 1 is a schematic perspective view of a disposable diaper according to a first embodiment of the present invention.
Figure 2:
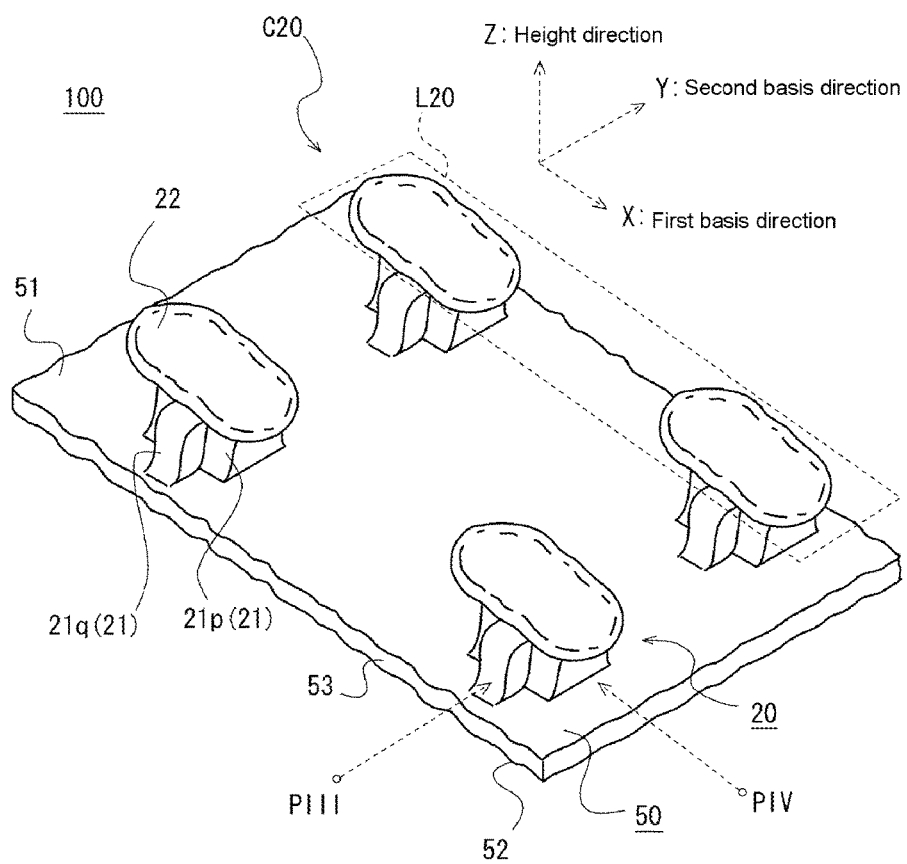
FIG. 2 is a schematic perspective view for showing the configuration of a surface fastener according to a first embodiment of the present invention.
Figure 3:
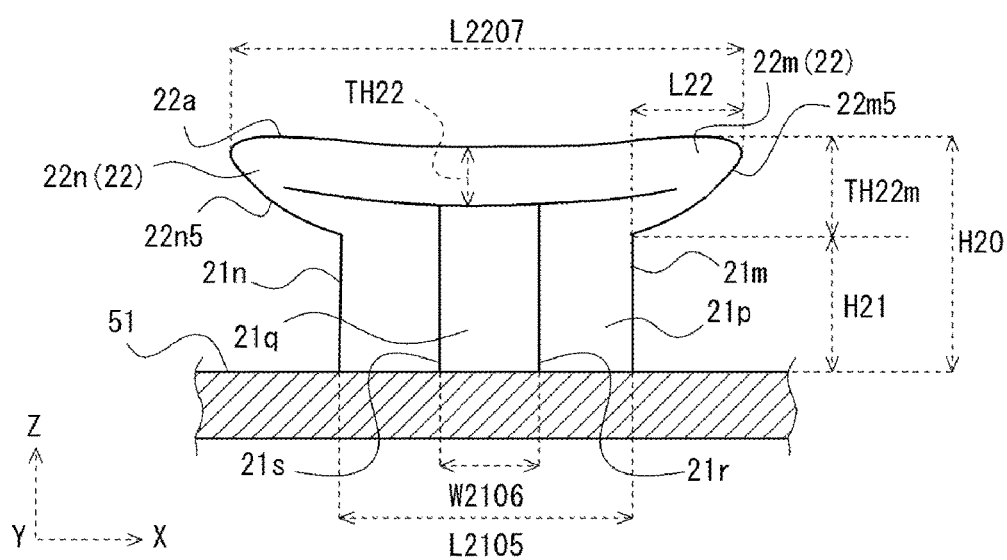
FIG. 3 is a schematic diagram illustrating an elongation side of an engagement element of a surface fastener according to a first embodiment of the present invention.
Figure 4:
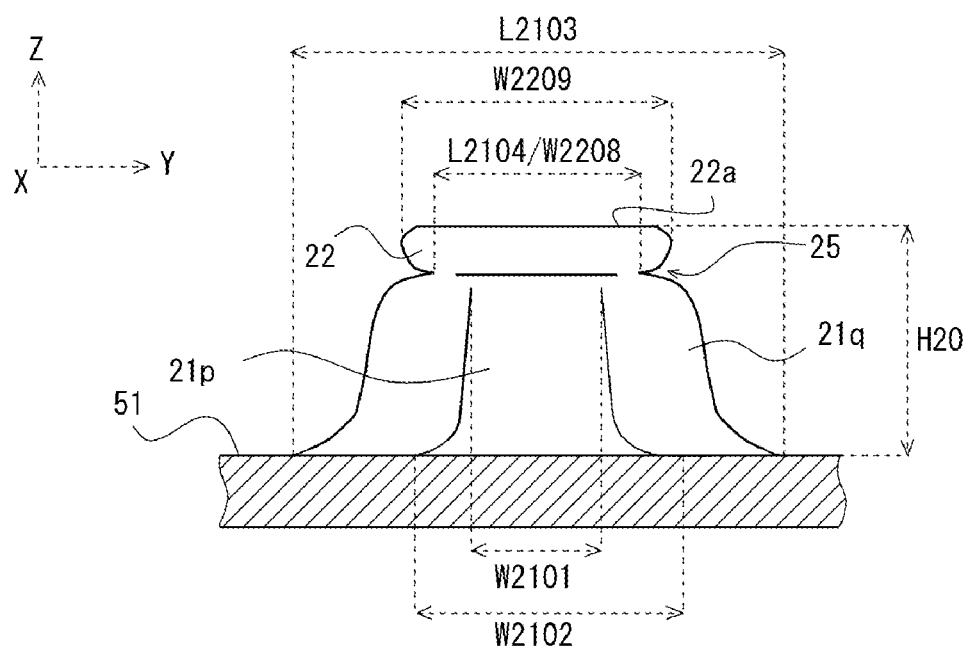
FIG. 4 is a schematic diagram illustrating a narrower side of an engagement element of a surface fastener according to a first embodiment of the present invention.
Figure 5A:
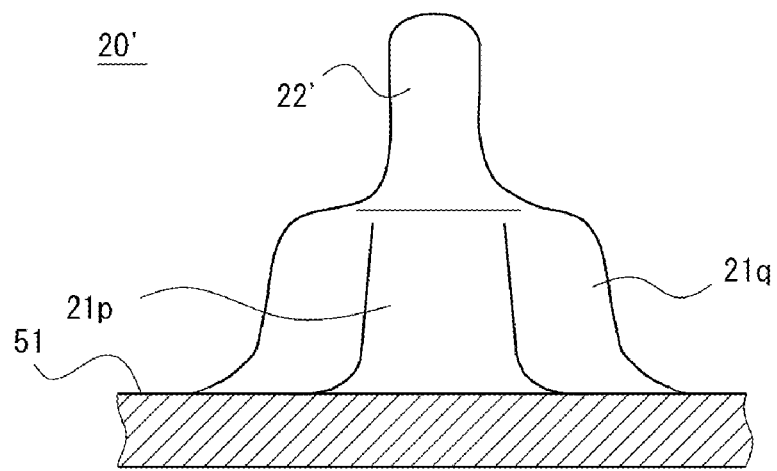
FIG. 5(a) and FIG. 5(b), collectively referred to as FIG. 5 are diagrams for illustrating a manner of plastic deformation of an engagement element of a surface fastener according to a first embodiment of the present invention.
Figure 5B:
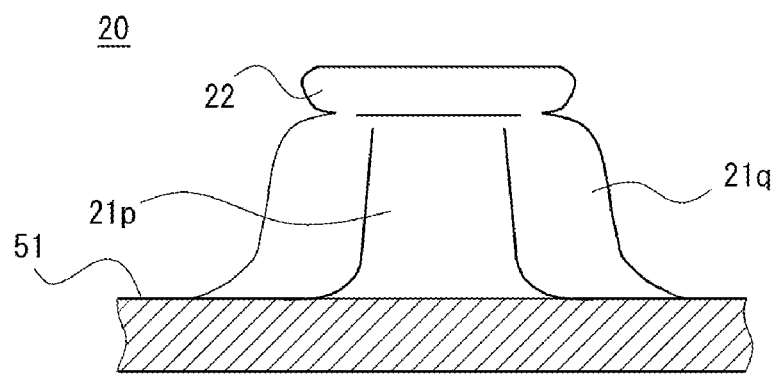
Figure 6:
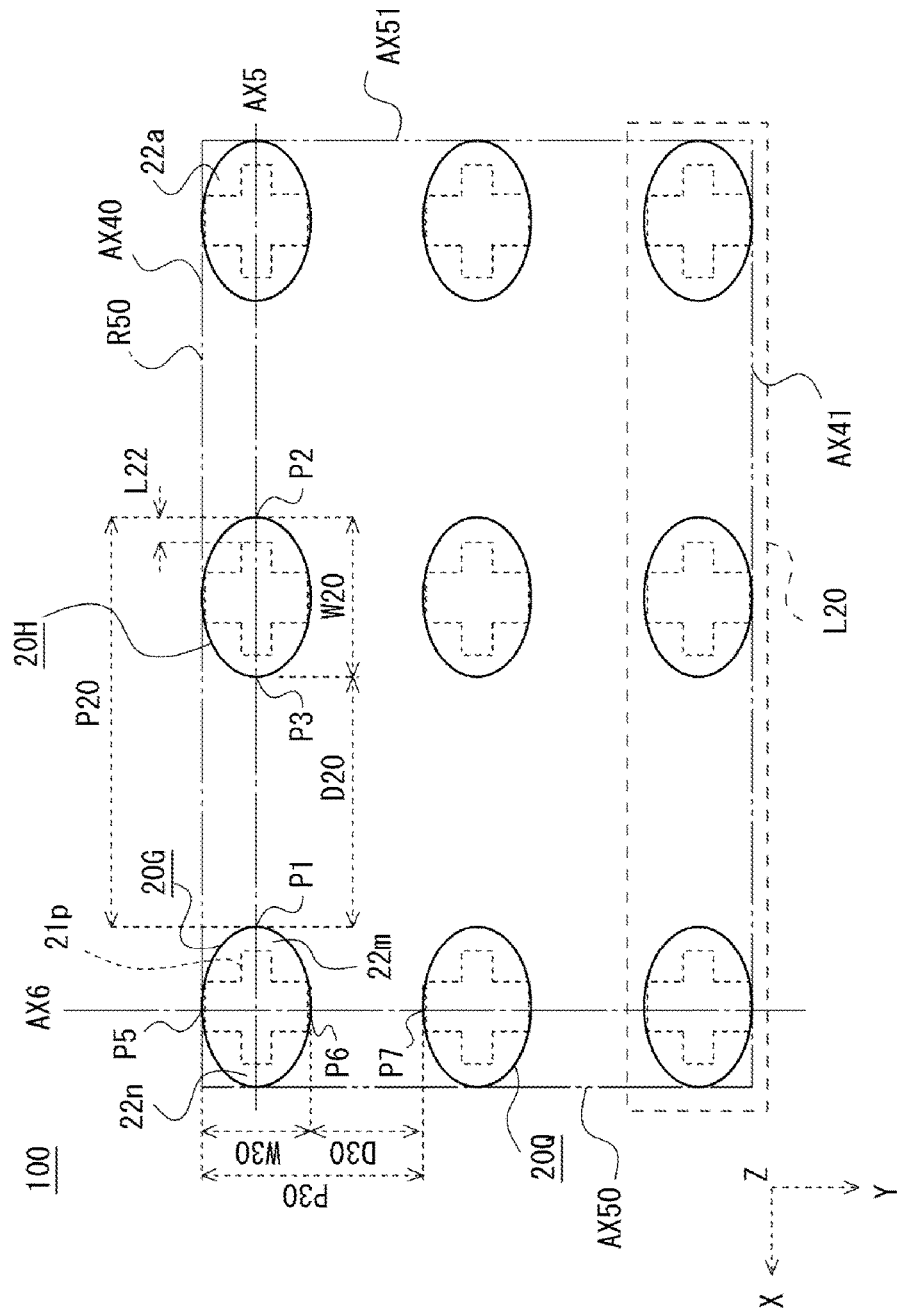
FIG. 6 is a schematic top view for illustrating the configuration of a surface fastener according to a first embodiment of the present invention.

The first embodiment will be described with reference to FIG. 1 to FIG. 6. FIG. 1 is a schematic perspective view of a disposable diaper. FIG. 2 is a schematic partially expanded perspective view of a surface fastener. FIG. 3 is a schematic diagram illustrating an elongation side of an engagement element of a surface fastener. FIG. 4 is a schematic diagram illustrating a shorter side of an engagement element of a surface fastener. FIG. 5 is a diagram for illustrating a manner of plastic deformation of an engagement element of a surface fastener. FIG. 6 is a schematic partially expanded top view of a surface fastener.

A disposable diaper 200 illustrated in FIG. 1 may be a commonly used disposable diaper having a diaper body 201 and a pair of attachment tapes 202, and is a composite product configured from a combination of various functional members consisting of a surface member, an absorption member, a waterproof protect member, a stretch member and so on. The diaper body 201 has a front covering 201a which covers the lower trunk of a human, i.e. near the groin from the front side; a back covering 201b which covers the lower trunk of a human, i.e. the buttocks of a human from the back side; and a bottom covering 201c which couples between the front covering 201a and the back covering 201b and which covers the crotch of a human. A pair of guard walls 201r for preventing a leak of liquid etc. while the disposable diaper 200 being used by a human are provided across the total length between the front covering 201a and the back covering 201b and at the internal side surface of the diaper body 201 at which side the diaper body 201 touches a human. The absorption members etc. are intensely arranged in a region between the guard walls 201r. It should be noted that the terms of front, back, and bottom indicated here should be understood based on a person who is wearing the disposable diaper 200.

The pair of attachment tapes 202a, 202b are attached to the right and left sides 201am, 201an which are at the upper end side of the front covering 201a. The male surface fastener 100 is fixed to each attachment tape 202 by any securing method such as gluing and so on. A female surface fastener may preferably be provided at a defined location within the diaper body 201 corresponding to the male surface fastener 100. The female surface fasteners may take any configuration only if it is configured to be engageable with the male surface fastener. As to representative examples for the female surface fasteners, there are a nonwoven fabric including plural loops, a weaved fabric, a knitted fabric or a felt fabric in which plural loops are formed on the surface through gigging/raising etc., not limited thereto though.

In the present example, the diaper body 201 itself made of a nonwoven fabric having a thickness of 0.1 mm to 0.3 mm and a weight of 10 to 20 g/cm$^2$ is used for the female surface fastener. Even in such a case, the male surface fasteners 100 can two-dimensionally engage with the nonwoven fabric, i.e. the female surface fastener, with enough strength so that simplification and costdown can be fascilitated as other separate female surface fasteners being not provided onto the disposable diaper 200.

Needless to say that it may also be preferable to provide other separate female surface fasteners onto the disposable diaper 200 and to allow the male surface fastener 100 disclosed herein to engage with that female surface fastener. The disposable diapers 200 may not necessarily be one-time only disposable types, and they can be diapers which can endure several times or even several years of use. The instant specification does not describe a method for producing the disposable diapers 200 in detail as it is widely known in the filed of disposable diapers.

The nonwoven fabric of the disposable diaper 200 may take any configurations, but it may preferably have a thickness of 0.1 mm to 0.3 mm and a weight of 10 to 20 g/cm$^2$. The nonwoven fabric may be mass-produced at lower cost because fibers are not weaved or knitted like weaved fabrics or knitted fabrics. The fibers used for forming the nonwoven fabric may not necessarily be limited to cellulose fibers. Aramid fibers, glass fibers, nylon fibers, vinylon fibers, polyester fibers, polylefins fibers, rayon fibers and so on may be used, for example. Any known manufacturing method for the nonwoven fabrics may be used.

A purchaser of the disposable diaper 200 may grasp the attachment tape 202, i.e. the male surface fastener 100, and push it against the nonwoven fabric forming the outer surface of the back covering 201b of the disposable diaper 200 so that the male surface fastener 100 engage with the nonwoven fabric. There is no need for the purchaser of the disposable diaper 200 to attach the male surface fastener 100 to a predetermined planar region or an accuracy required thereto is relaxed for the purchaser of disposable diapers 200 so that the usability of disposable diapers 200 would be improved. Sufficient engagement power may be more surely obtained by widening the area of the male surface fastener 100 more than normally required which is to be provided on the attachment tape 202. With respect to the piece of the male surface fastener 100 to be attached to the attachment tape 202, the size of the male surface fastener 100 may typically be 2 to 16 mm$^2$ It would be quite natural that the size of the male surface fastener correlates to the diaper size, and thus that size may preferably be larger if it is used for nursing care diapers interad of baby diapers.

The pair of attachment tapes 202a, 202b may be provided at the left and right sides at the upper end side of the back covering 201b, and they may be pushed against the nonwoven fabric forming the outer surface of the front covering 201a so that the male surface fastener 100 will engage with that nonwoven fabric.

The configuration of the male surface fastener 100 will be described with reference to FIG. 2. As shown in FIG. 2, the male surface fastener 100 is a member in which a group C20 of the resin-made engagement elements 20 is located on a plate-like resin-made sheet 50. The engagement elements 20 are regularly arranged to construct the group C20 of the engagement elements 20. The number of engagement elements 20 provided on the top surface 51 of the sheet 50 per 1 cm$^2$ may be 230 to 280 pieces even though the instant application does not illustrate the countless micro engagement elements 20 being provided on the sheet 50.

The male surface fastener 100 may typically be made of a resin and have enough flexibility, and it preferably be made of nylon, polyester, polypropylene, polyethylene, thermoplastic elastomer and so on. The top view shape of the sheet 50 may typically be a square but not limited to, and it may be other shapes such as a polygon including a triangle and so on and a circle, for example. The sheet 50 has a pair of main surfaces including a top surface 51 and a bottom surface 52 and has a side surface 53 defining its periphery. The top surface 51 of the sheet 50 is a fastening side in which a plurality of engagement elements 20 are provided, and the bottom surface 52 of the sheet 50 is a fixing side at which the male surface fastener 100 is fixed to other members. The sheet 50 may not necessarily be a plate-like and a number of projections and recesses can be provided thereto.

The engagement elements 20 are regularly arranged on the top surface 51 of the sheet 50. Specifically, the engagement elements 20 are aligned at a constant interval along X-axis (a first basis direction for defining a plane in which the sheet 50 exists) so that the engagement elements 20 form a line and the engagement element line L20 is constructed. The engagement element lines L20 are aligned at a constant interval along Y-axis (a second basis direction for defining a plane in which the sheet 50 exists) so that the group C20 of the engagement elements 20 is established. In this example, X-axial direction is equal to an extending direction of the engagement head, Y-axial direction is equal to a direction that is substantially parallel to the sheet 50 and is perpendicular to the x-axial direction. Z-axial direction is a direction that is perpendicular to both of the x-axis and y-axis.

As shown in FIG. 2, the engagement element 20 is a projection including a pillar 21 and an engagement head 22. The pillar 21 rises vertically from the top surface 51 of the sheet 50, and its cross-section is shaped like a cross. The pillar 21 is shaped like a cross in cross-section so that an amount of resin to be used may be reduced compared to a rectangular cross-sectional shape while maintaining a sufficient mechanical strength of the pillar 21.

The engagement head 22 is a plate-like thin portion that is provided on the top end of the pillar 21 and expands along the x-axial direction from the top end of the pillar 21 in both directions. The top view shape of the engagement head 22 is like a rectangular that is elongated in the x-axial direction. FIG. 3 illustrates a side view of the engagement element 20 seen from a viewpoint PIII shown in FIG. 2. FIG. 4 illustrates a side view of the engagement element 20 seen from a viewpoint PIV shown in FIG. 2. More detail descriptions will follow with respect to the configuration of the engagement element 20 with reference to FIGS. 3 and 4 additionally to FIG. 2.

As shown in FIGS. 2-4, the pillar 21 includes a first pillar 21p and a second pillar 21q which vertically stand on the top surface 51 of the sheet 50 so as to form a shape of cross, and therefore its cross-section is shaped like an alphabet of X. The first pillar 21p and the second pillar 21q are pillars each having a predetermined width, a predetermined length, and a predetermined height. The first pillar 21p is elongated in x-axis and has a narrowed width in y-axis. The second pillar 21*q* is elongated in y-axis and has a narrowed width in x-axis. The cross-section of the pillar 21 is shaped like a cross across the height from the base end to the top end of the pillar 21, not limited thereto though.

As shown in FIG. 3, the engagement head 22 is a plate-like portion that is elongated in x-axial direction and has a narrowed width in y-axial direction. The engagement head 22 expands in opposite direction from the pillar 21 along x-axial direction so as to include a one-side expanded portion 22*m* and an opposite side expanded portion 22*n*. The one-side expanded portion 22*m* is upwardly curved as it extends away from the pillar 21 or is oriented obliquely upwardly, and a similar explanation can apply to the opposite side expanded portion 22*n*. The both ends of the elongated engagement head 22 are upwardly curved so that the loop(s) can be preferably caught by each expanded portion. The engagement head 22 may be obliquely downwardly oriented to be cast down so that the engagement power may be enhanced.

Furthermore, the one-side expanded portion 22*m* is gradually thinned as it extends away from the pillar 21, and a same explanation can apply to the opposite side expanded portion 22*n*. The ends of the elongated engagement head 22 are tapered toward its tips so that the loops can be preferably caught by each expanded portion of the engagement head 22. It should be noted that the space between the bottom surface 22*m*5 and the top surface 51 changes to be gradually greater as the bottom surface 22*m*5 of the one-side expanded portion 22*m* is curved upwardly like an arc. This feature can similarly apply to the bottom surface 22*n*5 of the opposite side expanded portion 22*n*.

The top surface 22*a* of the engagement head 22 is substantially flat, but it is configured to be an arc surface in which the central portion along x-axial direction is depressed to match the curved manner of the ends of the elongated engagement head 22 in x-axial direction as described above. The top surface 22*a* of the engagement head 22 is formed to be substantially flat so that pang given to a skin of a human may possibly be suppressed.

The first pillar 21*p* forming the pillar 21 has a pair of vertical side surfaces 21*m*, 21*n* which vertically rise from the top surface 51 of the sheet 50 and vertically extend to reach the engagement head 22. The second pillar 21*q* has a pair of vertical side surfaces 21*r*, 21*s* which vertically rise from the top surface 51 of the sheet 50 and vertically extend towards the engagement head 22. The vertical side surfaces 21*m*, 21*n* and the vertical side surfaces 21*r*, 21*s* are side surfaces perpendicularly crossing the x-axis and extending along the y-axis.

The one-side expanded portion 22*m* of the engagement head 22 projects upwardly obliquely from the vertical side surface 21*m* away from the pillar 21 in the x-axial direction. The opposite side expanded portion 22*n* of the engagement head 22 projects upwardly obliquely from the vertical side surface 21*n* away from the pillar 21 in the x-axial direction. The respective projecting length L22 of the one-side expanded portion 22*m* and the opposite side expanded portion 22*n* are substantially equal, but not limited to and possibly there may be a difference between them.

As show in FIG. 4, the width of the first pillar 21*p* becomes gradually smaller from the base end side to the top end side of the first pillar 21*p* where a maximum width W2102 is at the bottom position of the base end and a minimum width W2101 is at the top position of the top end. As shown in FIG. 4, the length of the second pillar 21*q* becomes gradually smaller from the base end to the top end side of the second pillar 21*q* where a maximum length L2103 is at the bottom position of the base end and a minimum length L2104 is at the top position of the top end. As illustrated in FIG. 3, the length of the first pillar 21*p* has a constant length L2105 across a range between the base end and the top end of the first pillar 21*p*. The width of the second pillar 21*q* has a constant width W2106 across a range between the base end and the top end of the second pillar 21*q*.

As shown in FIG. 3, the length of the engagement head 22 gradually increases in accordance with an increase in upward distance from the top end of the pillar 21 where its maximum length L2207 is longer than the length L2105 of the first pillar 21*p* and the maximum length L2104 of the second pillar 21*q*. As shown in FIG. 4, the width of the engagement head 22 gradually increases in accordance with an increase in upward distance away from the pillar 21 side, and it gradually decreases after passing through an intermediate point. The engagement head 22 has the minimum width W2208 at its coupling end at the pillar 21 side and the maximum width W2209 at the intermediate point between the top end of the pillar 21 and the top surface 22*a* of the engagement head 22.

As shown in FIG. 4, the length of the second pillar 21*q* in y-axial direction is greater than the width of the engagement head 22, and the engagement head 22 is placed on the second pillar 21*q* such that a V-like depression 25 is formed between the second pillar 21*q* and the engagement head 22.

As shown in FIG. 4, the width of the first pillar 21*p* becomes larger from the width W2101 to the width W2102 from the top end side towards the bottom end side of the first pillar 21*p*. On the other hand, the length of the second pillar 21*q* becomes longer from the length L2104 to L2103 from the top end side to the base end side of the second pillar 21*q*. The first pillar 21*p* and the second pillar 21*q* are configured as such so that the stiffness and mechanical strength of each pillar is enhanced, thereby making it more difficult to lay the pillar 21.

As shown in FIG. 3, the maximum thickness TH22*m* of the one-side expanded portion 22*m* is greater than the thickness TH22 of the engagement head 22 at the intermediate point between one end and the other end, thereby enough mechanical strength of the one-side expanded portion 22*m* is secured. This feature holds true for the opposite side expanded portion 22*n*. Even assuming that the thickness TH22 at the intermediate portion between one end and the other end of the engagement head 22 was decreased, a problem of strength may not be evident owing to the pillar 21 below.

The specific values of the dimensions illustrated in FIGS. 3 and 4 are as follows: the minimum width W2101 of the first pillar 21*p* may typically be 0.06 to 0.12 mm and the maximum width W2102 may typically be 0.2 to 0.4 mm. The maximum length L2103 of the second pillar 21*q* may typically be 0.3 to 0.5 mm and the minimum length L2104 may typically be 0.1 to 0.3 mm. The length L2105 of the first pillar 21*p* may typically be 0.15 to 0.3 mm. The width W2106 of the second pillar 21*q* may typically be 0.05 to 0.1 mm. The length L2207 of the engagement head 22 may typically be 0.3 to 0.5 mm. The minimum width W2208 of the engagement head 22 is equal to the minimum length L2104 of the second pillar 21*q*. The maximum width W2209 of the engagement head 22 may typically be 0.1 to 0.3 mm.

The height H20 of the engagement element 20 may typically be 0.2 to 0.3 mm. The thickness TH22 of the intermediate portion of the engagement head 22 may typically be 0.03 to 0.1 mm. The maximum thickness TH22*m* of the expanded portion of the engagement head 22 may typically be 0.05 to 0.1 mm. The height H21 of the pillar 21 may typically be 0.15 to 0.25 mm.

The top surface 22a of the engagement element 20 is a substantially flat surface, and thus an extent of pang given to a human skin may be less even in a case where the height H20 of the engagement element 20 is increased more than a normal height. In this case, the engagement head 22 can sufficiently enter into the nonwoven fabric so that much adequate power would be secured possibly. The lengths and the widths of the first pillar 21p and the second pillar 21q are suitably regulated in accordance with the area of the top surface 22a of the engagement element 20 so that sufficient strength of the pillar 21 can be secured.

The male surface fastener 100 may be produced by injecting melted resin into a die and solidifying that resin. The engagement head 22 may be formed by plastically deforming a molded preform instead of being molded by a die. For example, a projection 22' of the molded product 20' to be the engagement head shown in FIG. 5(a) may be heated and deformed by a heating roller and so on so that it is shaped to be the plate-like engagement head 22 shown in FIG. 5(b). Any specific shape and position of placement for the projection 22' which is to be the engagement head may be adoptable, and similar configuration may be adoptable as the patent document 1 which is herein incorporated by reference. Any particular means and methods for plastically deforming the projection 22' which is to be the engagement element 20 may be utilizable.

Derail descriptions will be made with respect to the regular arrangement of the engagement elements 20 with reference to FIG. 6. Any regular arrangement of the engagement elements 20 may be usable and not necessarily limited to the illustrated example. The engagement elements 20 may be regularly arranged in a zigzag pattern in some cases. The engagement elements 20 may be regularly arranged in circles having different diameters in some cases. Some regions where the engagement elements 20 are not provided may be introduced discretely in a group of the regularly arranged engagement elements 20.

FIG. 6 illustrates an axis AX5 which is parallel to x-axis and an axis AX6 which is parallel to y-axis. The axis AX5 is an axis which matches the elongation direction of the first pillar 21p, the axis AX5 being located at the middle in width of the top surface 22a of the engagement head 22 and defining the maximum length of the top surface 22a of the engagement head 22. The axis AX6 is an axis which matches the elongation direction of the second pillar 21q, the axis AX6 being located at the middle in the length of the top surface 22a of the engagement head 22 and defining the maximum width of the top surface 22a of the engagement head 22.

The engagement elements 20 laterally arranged side by side when FIG. 6 is viewed in front are respectively numbered and referenced as the engagement element 20G and the engagement element 20H, and the engagement elements 20 longitudinally arranged side by side when FIG. 6 is viewed in front are respectively numbered and referenced as the engagement element 20G and the engagement element 20Q, for the sake of explanation.

P1 represents an intersection at which the axis AX 5 intersects the outer circumference edge of the top surface 22a of the engagement head 22 which is at a side of the one-side expanded portion 22m of the engagement element 20G. P2 represents an intersection point which the axis AX5 intersects the outer circumference edge of the top surface 22a of the engagement head 22 which is at a side of the one-side expanded portion 22m of the engagement element 20H. P3 represents an intersection at which the AX5 intersects the outer circumference edge of the top surface 22a of the engagement head 22 which is at a side of the opposite side expanded portion 22n of the engagement element 20H. An interval between the intersection points P1 and P2 is represented by an interval P20, an interval between the intersection points P1 and P3 is represented by an interval D20, and an interval between the intersection points P2 and P3 is represented by an interval W20. The interval P20 corresponds to the lateral arrangement interval of the engagement elements 20. The interval D20 corresponds to the lateral separation distance of the engagement elements 20. The interval W20 corresponds to the length of the engagement head 22 of the engagement element 20.

P5 and P6 represent intersection points at which the axis AX6 intersect the outer circumference edge of the top surface 22a of the engagement head 22 of the engagement element 20G. The intersection point P5 represents an intersection point at which the axis AX6 intersects the outer circumference edge of the top surface 22a at the upper side in the printed FIG. 6. The intersection point P6 represents an intersection point at which the axis AX6, extending over the engagement element 20G from the intersection point P5, intersects the outer circumference edge at the other side of the top surface 22a at the lower side in the printed FIG. 6. P7 represents an intersection point at which the axis AX6 intersects the outer circumference edge of the top surface 22a of the engagement head 22 of the engagement element 20Q which is at the engagement element 20G side. An interval between the intersection point P5 and the intersection point P7 is represented by an interval P30, and an interval between the intersection point P5 and the intersection point P6 is represented by an interval W30, and an interval between the intersection point P6 and the intersection point P7 is represented by an interval D30. The interval P30 corresponds to the longitudinal arrangement interval of the engagement elements 20. The interval W30 corresponds to the width of the engagement head 22 of the engagement element 20. The interval D30 corresponds to the separation distance between the longitudinally arranged engagement elements 20.

In the present embodiment, the engagement elements 20 having the top surface 22a are much sparsely arranged on the top surface 51 of the sheet 50 compared to the prior distributions. Normally, preferred engagement power of the male surface fastener 100 will be secured by densely distributing the engagement elements 20 on the top surface 51 of the sheet 50. However, according to an analysis by the present inventor, it has turned out that higher density distribution of the engagement elements 20 is not always suitable for some applications, and some situations prefer the distribution/arrangement where the engagement elements 20 are arranged to have greater lateral and longitudinal intervals.

In view of FIG. 6 where the group C20 of the engagement elements 20 of lateral 3 pieces*longitudinal 3 pieces=total 9 pieces is provided, an area S1 represents an area of the fastening region R50 in the top surface 51 of the sheet 50 which corresponds to the arrangement area of the group C20 of the engagement elements 20, and an area S2 represents a sum of areas of the top surfaces 22a of the engagement heads 22 of the engagement elements 20 arranged in the fastening region R50. Under this condition, $0.05 \leq S2/S1 \leq 0.15$ is preferably satisfied. Accordingly, much sufficient engagement power would be obtained in relation to the female surface fastener of a nonwoven fabric and so on of the disposable diaper 200 and so on. In this technical field, it has been widely conducted to increase the number of engagement elements 20 in an effort to enhance the engagement power of the male surface fastener 100. The present inventor has achieved the unexpected result by conducting an attempt which is seemingly against this technical common knowledge suggested above.

The fastening region R50 corresponds to an imaginary region surrounding the regularly arranged engagement elements 20, in particular it is defined by lines tangent to the circumference edges of the top surfaces 22a of the engagement heads 22 of the outermost engagement elements 20 in the group C20 of the regularly arranged engagement elements 20 and which outline the group C20 of the engagement elements 20. In the present example, provided that the FIG. 6 paper is viewed in front, the fastening region R50 is determined by an imaginary line AX40 passing trough the outer circumference edges of the top surfaces 22a of the engagement heads 22 of the laterally arranged uppermost engagement elements 20; an imaginary line AX41 passing through the outer circumference edges of the top surfaces 22a of the engagement heads 22 of the laterally arranged lowermost engagement elements 20 in Y-axial direction; an imaginary line AX50 passing through the outer circumference edges of the top surfaces 22a of the engagement heads 22 of the longitudinally arranged leftmost engagement elements 20 in X-axial direction; and an imaginary line AX51 passing through the outer circumference edges of the top surfaces 22a of the engagement heads 22 of the longitudinally arranged rightmost engagement elements 20 in X-axial direction.

For example, with respect to the group of nine pieces of engagement elements 20 shown in FIG. 6, when the lateral arrangement interval P20 of the engagement elements 20 is 0.75 mm and the longitudinal arrangement interval P30 is 1.1 mm, the fastening region R50 can be 1.9 mm*2.5 mm=4.75 mm$^2$.

There may be no need to give a specific definition for the area of the top surface 22a of the engagement head 22 of the engagement element 20. However, in this example, considering the slightly rounded outer circumference edge of the top surface 22a of the engagement head 22, the area of the top surface 22a of the engagement head 22 is determined as an area within an outline/contour of the top surface 22a of the engagement head 22 which can be seen when viewing the surface fastener 100 in front as depicted in FIG. 6.

In this example, the area of the top surface 22a of one engagement head 22 is 0.08 mm$^2$, and the sum of areas of the top surfaces 22a of the engagement heads 22 of nine pieces of engagement elements 20 is 0.72 mm$^2$ When this sum of areas is divided by the area of the fastening region R50, the resulting outcome is 15% when expressed by %.

The relationship between the above-described intervals will be further described. It may be preferable to satisfy: interval W20<interval D20. Accordingly, sufficient separation distance for the laterally arranged engagement elements depicted in FIG. 6 can be obtained. Specifically, the interval W20 satisfies 0.2 mm<W20<0.4 mm, and the interval D20 satisfies 0.6 mm<D20<1.0 mm, preferably. The interval P20, which is equal to the sum of the interval D20 and the interval W20, preferably satisfies 1.0 mm≤P20≤1.2 mm.

Preferably, interval W30<interval D30 is satisfied. Accordingly, sufficient separation distance of the longitudinally arranged engagement elements depicted in FIG. 6 can be secured. In specific, the interval P30 satisfies 0.7 mm≤P30≤0.9 mm, the interval W30 satisfies 0.15 mm<W30<0.35 mm, and the interval D30 satisfies 0.35 mm<D30<0.75 mm, preferably.

By the use of the male surface fastener 100 of the present embodiment, as proved by examples described below, much adequate engagement power can be achieved particularly for the nonwoven fabric which is an example of the female surface fastener. In such a case, as stated at the beginning, there is no requirement to provide a separate female surface fastener for the disposable diaper 200, and the nonwoven fabric of the body of the disposable diaper 200 can be used as the female surface fastener. This would facilitate the simplification and costdown of the manufacturing process of products for the users of the male surface fasteners 100, and desired engagement power based on the engagement between the male surface fastener 100 and female surface fastener can be secured. As no sharpness is present at the top surface 22a of the engagement elements 20, it is particularly suitable for the use of diapers.

Second Embodiment

The second embodiment will be described with reference to FIGS. 7 and 8. FIG. 7 illustrates schematic side and top diagrams of an engagement element of a surface fastener. FIG. 8 is a schematic partially expanded top view of a surface fastener. In this embodiment, engagement elements having a different shape compared to that of the first embodiment, so-called mushroom types are employed. Even in such a case, it is expected that an effect similar to the one described at the first embodiment can be obtained. The mushroom type engagement elements 20 have no directionality of engagement so that it can possibly more preferably engage with the female surface fastener of the nonwoven fabric and so on.

Figure 7A:
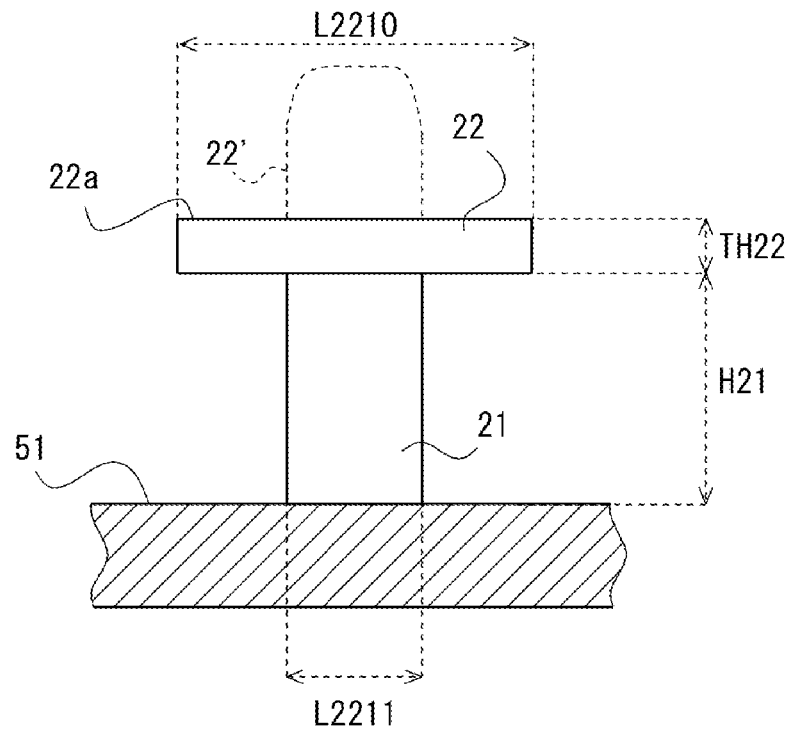
FIG. 7(a) and FIG. 7(b), collectively referred to as FIG. 7 illustrate schematic side and top diagrams of an engagement element of a surface fastener according to the first embodiment of a second embodiment of the present invention.
Figure 7B:
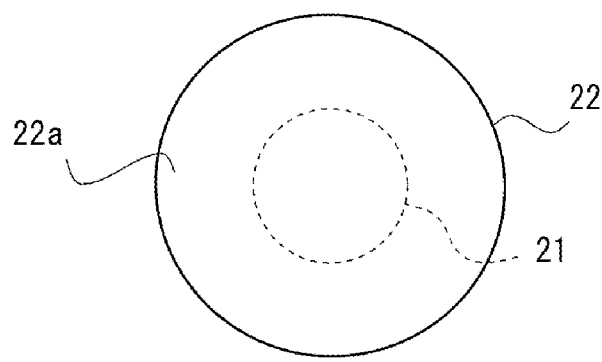
Figure 8:
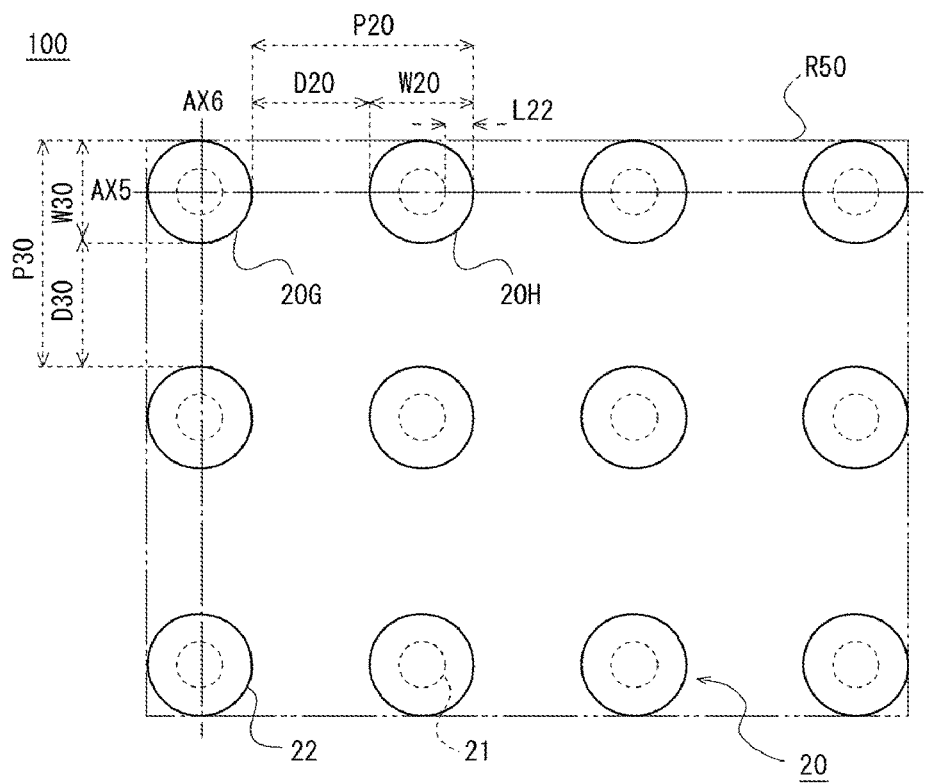
FIG. 8 is a schematic partially expanded top view for illustrating the configuration of a surface fastener according to a second embodiment of the present invention.

As shown in FIG. 7(a), the mushroom type engagement element 20 includes a column-like pillar 21 and a disk-like engagement head 22 coupled to the top end of the pillar 21. The pillar 21 is a cylinder vertically standing on the top surface 51 of the sheet 50. The engagement head 22 expands radially outwardly from the top end of the pillar 21 and uniformly around the entire circumference of the pillar 21. Similar to the first embodiment, the engagement head 22 is formed by heating and melting the projection 22' illustrated in dots. As shown in FIG. 7(b), the the cylindrical pillar 21 and the disk-like engagement head 22 are concentrically arranged substantially.

As shown in FIG. 8, the intervals may be set out similarly to the first embodiment. The mushroom type engagement element 20 has no directionality unlike the engagement element 20 configured as shown in the first embodiment. Therefore, interval W20=interval W30 may be naturally satisfied, and further interval P20=interval P30 and interval D20=interval D30 may be satisfied.

Descriptions will be made with reference to FIG. 8. The fastening region R50 in the top surface 51 of the sheet 50 where the group of the engagement elements 20 of lateral 4 pieces*longitudinal 3 pieces=total 12 pieces is located is represented by an area S1, and the sum of areas of the top surfaces 22a of the engagement heads 22 of the engagement elements 20 arranged in the fastening region R50 is represented by an area S2. Similar to the first embodiment, 0.05≤S2/S1≤0.15 is preferably satisfied.

It may be preferable to satisfy interval W20<interval D20. Accordingly, sufficient separation distance for laterally arranged engagement elements can be secured. Specifically, interval W20 satisfies 0.2 mm<W20<0.4 mm, and the interval D20 preferably satisfies 0.6 mm<D20<1.0 mm. The interval P20, which is equal to the sum of interval D20 and interval W20, may preferably satisfy 1.0 mm≤P20≤1.2 mm.

Preferably, interval W30<interval D30 is satisfied. Accordingly, sufficient separation distance can be secured for longitudinally arranged engagement elements 20. Specifically, the interval P30 satisfies 0.7 mm≤P30≤0.9 mm, and the interval W30 satisfies 0.15 mm<W30<0.35 mm, and the interval D30 preferably satisfies 0.35 mm<D30<0.75 mm.

Examples

Figure 9:
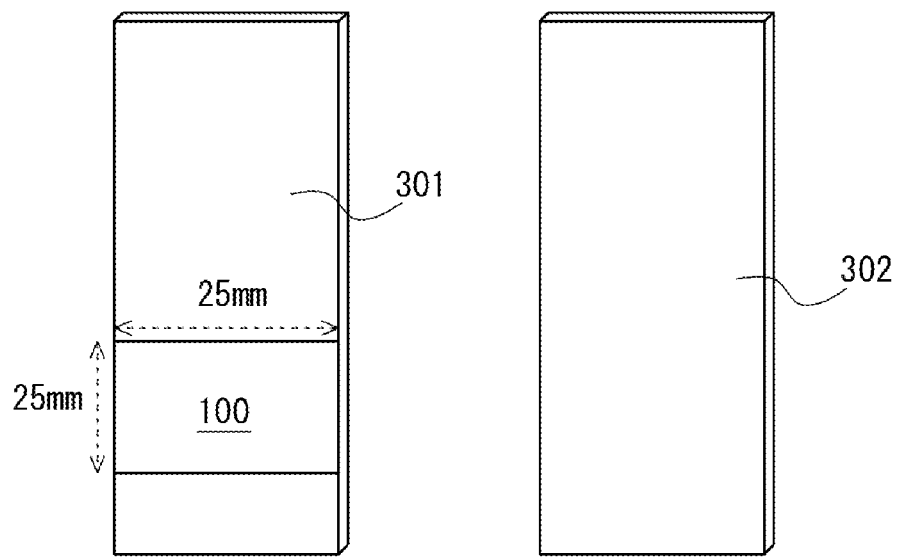
FIG. 9 is a diagram showing a specimen that is used for a tensile test for a surface fastener according to an example of the present invention.
Figure 10:
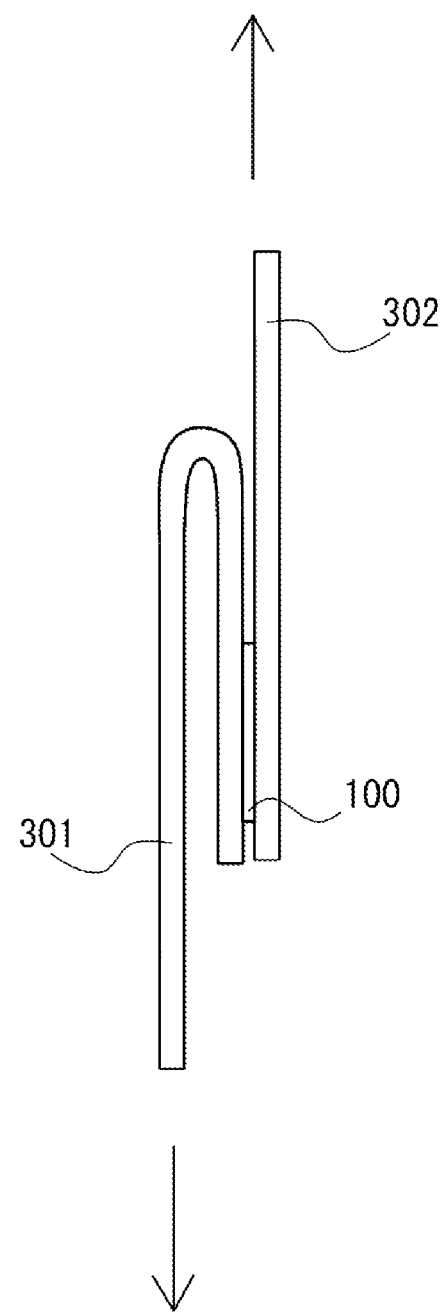
FIG. 10 is a diagram showing a method of a tensile test for a surface fastener according to an example of the present invention.
Figure 11:
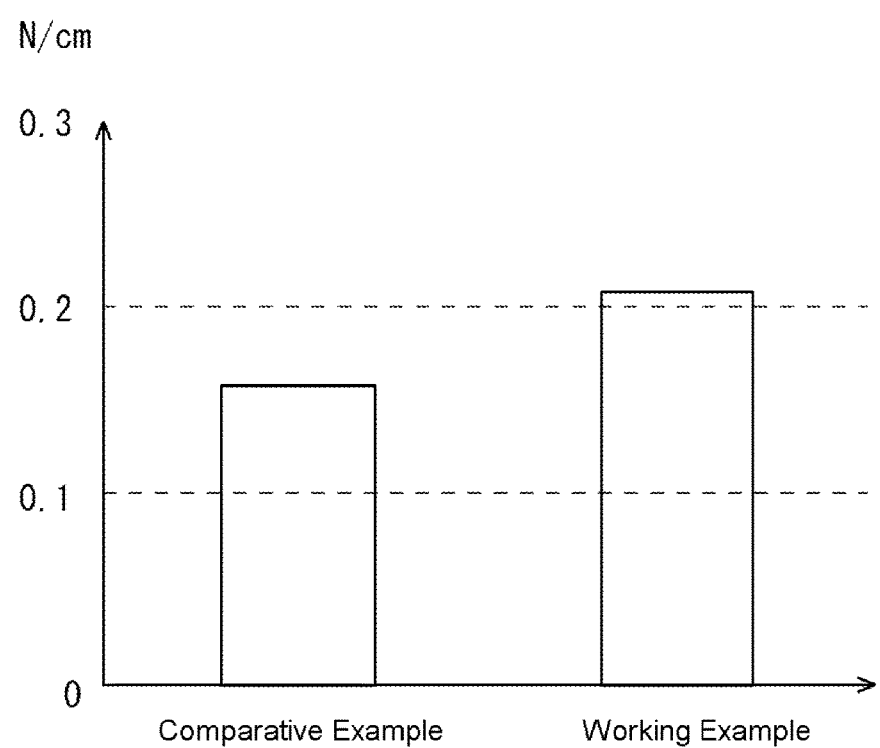
FIG. 11 is a graph showing an outcome of a tensile test for a surface fastener according to an example of the present invention.

Examples will be described with reference to FIG. 9 to FIG. 11. FIG. 9 is a diagram showing a specimen that is used for a tensile test for a surface fastener. FIG. 10 is a diagram showing a method of a tensile test for a surface fastener. FIG. 11 is a graph showing an outcome of a tensile test for a surface fastener.

Firstly, the surface fasteners according to comparative example and working example under the condition shown in Chart 1 were manufactured. In the comparative example and the working example, the engagement elements 20 configured as described in the first embodiment and particularly illustrated in FIG. 2 were adopted. In the comparative example, the engagement elements 20 were densely arranged and, on the other hand, the engagement elements 20 were sparsely arranged in the working example. With respect to the manufacturing of the surface fastener, the molded product was firstly produced by a die, and then the projection was heated and melted as described with reference to FIG. 5 so that the engagement head was formed.

CHART 1

|  | Comparative example | Working example |
|---|---|---|
| Interval P20 (mm) | 0.6 | 1.11 |
| Interval D20 (mm) | 0.1 | 0.73 |
| Interval W20 (mm) | 0.5 | 0.38 |
| Projection height L22 (mm) | 0.15 | 0.09 |
| Interval P30 (mm) | 0.6 | 0.76 |
| Interval W30 (mm) | 0.3 | 0.27 |
| Interval D30 (mm) | 0.3 | 0.49 |
| S1: Arrangement area of group of engagement elements (mm$^2$) | 100 | 100 |
| Area of top surface of one engagement head (mm$^2$) | 0.12 | 0.08 |
| The number of engagement elements per 1 cm$^2$ | 278 pieces | 119 pieces |
| S2: Sum of areas of top surfaces of engagement heads | 33.36 | 9.52 |
| Density of engagement elements (S2/S1*100) | 33% | 10% |

Common parameters between the comparative example and the working example are as follows. The thickness of the sheet 50 of the male surface fastener 100 was equal to 0.1 mm. With respect to the engagement element 20, it was configured as follows: W2101=0.09 mm, W2102=0.26 mm, L2103=0.39 mm, L2104=0.22 mm, L2207=0.4 mm, W2209=0.27 mm, H21=0.18 mm, TH22m=0.07 mm, H20=0.25 mm. Resin material of polypropylene was commonly used between the comparative example and the working example to produce the male surface fasteners 100 under the identical condition.

The peel strength of the surface fastener according to the comparative example and the working example was tested as follows. The surface fastener speciments were sized to be square pieces of longitudinal 25 mm*lateral 25 mm. As shown in FIG. 9, the male surface fastener 100 was adhered and fixed to a plate member 301 of a nonwoven fabric and so on, and a nonwoven fabric 302 having the same size as the plate member 301 was prepared. Next, the plate member 301 and the nonwoven fabric 302 were piled via the male surface fastener 100 so that the male surface fastener 100 engages with the nonwoven fabric 302, thereby a specimen being prepared. Next, the tensile test for the speciments were performed using a commonly used tensile test machine. It should be noted that the tensile test machine used in this cases was an all-purpose tensile test machine manufactured by INSTRON Corporation at 2001. The test measurements were shown in a graph of FIG. 11. As apparent from the measurements in FIG. 11, according to the present examples, higher peel strength was obtained compared to the comparative example. The nonwoven fabric having thickness 0.2 mm and weight 13 g/cm$^2$ was used.

Based on the above teachings, the skilled person in the art could add various modifications to the respective embodiments. There should be no limitation on the types of the engagement elements, and other undisclosed configuration may be used. The other member with which the surface fastener engages should not be limited to the nonwoven fabric and other engagement members can be used, including an engagement member on which a plurality of loops are provided. The reference numbers in claims are just for reference and should not be utilized for narrowly construing the claimed scope.

REFERENCE SIGNS LIST

20: engagement element
21: pillar
21m: vertical side surface
21n: vertical side surface
21p: first pillar
21q: second pillar
21r: vertical side surface
22: engagement head
22a: top surface
22m: expanded portion at one end side
22m5: bottom surface
22n: expanded portion at the other end side
22n5: bottom surface
25: depression
50: sheet
51: top surface
52: bottom surface
53: side surface
100: male surface fastener
200: disposable diaper
201: diaper body
202: attachment tape
301: plate member
302: nonwoven fabric
R50: fastening region

The invention claimed is:

1. A male surface fastener for use with a non-woven fabric, comprising:
 a sheet having a main surface; and
 a group of engagement elements configured to be engaged with the non-woven fabric, the engagement elements being regularly arranged in a first direction and a second direction which are parallel to the main surface of the sheet, each of the engagement elements having a pillar that stands on the main surface of the sheet and an engagement head that is expanded over the main surface from a top end of the pillar, each engagement head being elongated in the first direction and having a narrower width in the second direction, wherein the second direction is orthogonal to the first direction, wherein $0.05 \leq S2/S1 \leq 0.15$ is satisfied where S1 represents an area of a fastening region of the main surface wherein the group of engagement elements is located in said fastening region, and S2 represents a sum of areas of top surfaces of the engagement heads of the engagement elements of the group of engagement elements located in said fastening region, W20<D20 being satisfied where D20 represents a separation distance between adjacent engagement heads along the first direction, and W20 represents a maximum width of the engagement head along the first direction;

W30<D30 being satisfied where D30 represents a separation distance between adjacent engagement heads along the second direction, and W30 represents a maximum width of the engagement head along the second direction;

the maximum width W20 satisfying 0.2 mm<W20<0.4 mm or the separation distance D20 satisfying 0.6 mm<D20<1.0 mm; and the maximum width W30 satisfying 0.15 mm<W30<0.35 mm or the separation distance D30 satisfying 0.35 mm<D30<0.75 mm.

2. The male surface fastener according to claim 1, wherein the pillar has a first pillar and a second pillar which stand on the main surface so that the pillar is cross-shaped in a cross-section taken between a base end and the top end of the pillar, and the engagement head is a plate-like thin portion having a pair of expanded portions expanding from the pillar along an elongation direction of the first pillar, a space being defined between each of the expanded portions and the main surface of the sheet.

3. The male surface fastener according to claim 1, wherein an arrangement interval P20 for adjacent engagement elements in the first direction satisfies 1.0 mm≤P20≤1.2 mm.

4. The male surface fastener according to claim 1, wherein an arrangement interval P30 for adjacent engagement elements in the second direction satisfies 0.7 mm≤P3≤0.9 mm.

5. A combination of a male surface fastener and a non-woven fabric, the male surface fastener comprising:

a sheet having a main surface; and a group of engagement elements configured to be engaged with the non-woven fabric, the engagement elements being regularly arranged in a first direction and a second direction which are parallel to the main surface of the sheet, each of the engagement elements having a pillar that stands on the main surface of the sheet and an engagement head that extends over the main surface from a top end of the pillar, each engagement head being elongated in the first direction and having a narrower width in the second direction, wherein the second direction is orthogonal to the first direction, wherein $0.05 \leq S2/S1 \leq 0.15$ is satisfied where S1 represents an area of a fastening region of the main surface wherein the group of engagement elements is located in said fastening region, and S2 represents a sum of areas of top surfaces of the engagement heads of the engagement elements of the group of engagement elements located in said fastening region, the top surface of the engagement heads being substantially flat, W20<D20 being satisfied where D20 represents a distance between adjacent engagement heads along the first direction, and W20 represents a maximum width of the engagement head along the first direction, W30<D30 being satisfied where D30 represents a distance between adjacent engagement heads along the second direction, and W30 represents a maximum width of the engagement head along the second direction, the maximum width W20 satisfying 0.2 mm<W20<0.4 mm and the separation distance D20 satisfying 0.6 mm<D20<1.0 mm, and the maximum width W30 satisfying 0.15 mm<W30<0.35 mm and the separation distance D30 satisfying 0.35 mm<D30<0.75 mm.

6. The combination according to claim 5, wherein an arrangement interval P20 for engagement elements in the first direction satisfies 1.0 mm≤P2≤1.2 mm.

7. The combination according to claim 6, wherein an arrangement interval P30 for engagement elements in the second direction satisfies 0.7 mm≤P30≤0.9 mm.

8. The combination according to claim 5, wherein an arrangement interval P20 for engagement elements in the first direction satisfies 1.0 mm≤P20≤1.2 mm.

9. The combination according to claim 8, wherein an arrangement interval P30 for engagement elements in the second direction satisfies 0.7 mm≤P30≤0.9 mm.

* * * * *

UNITED STATES PATENT AND TRADEMARK OFFICE
CERTIFICATE OF CORRECTION

PATENT NO. : 10,278,876 B2
APPLICATION NO. : 14/437149
DATED : May 7, 2019
INVENTOR(S) : Ayumi Fujisaki et al.

Page 1 of 1

It is certified that error appears in the above-identified patent and that said Letters Patent is hereby corrected as shown below:

In the Specification

In Column 5, Line 15, delete "fascilitated" and insert -- facilitated --, therefor.

In Column 5, Line 36, delete "polylefins" and insert -- polyolefins --, therefor.

In Column 12, Line 44, delete "the the"" and insert -- the --, therefor.

In Column 13, Line 65, delete "speciments" and insert -- specimens --, therefor.

In Column 14, Line 7, delete "speciments" and insert -- specimens --, therefor.

In the Claims

In Column 15, Line 46, in Claim 4, delete "0.7 mm≤P3≤0.9 mm." and insert -- 0.7 mm≤P30≤0.9 mm. --, therefor.

In Column 16, Line 41, in Claim 6, delete "1.0 mm≤P2≤1.2 mm." and insert -- 0.1 mm≤P20≤1.2 mm. --, therefor.

Signed and Sealed this
Sixteenth Day of July, 2019

Andrei Iancu
*Director of the United States Patent and Trademark Office*